（12）United States Patent
Dalmia et al.

(10) Patent No.: US 7,601,233 B2
(45) Date of Patent: *Oct. 13, 2009

(54) ELECTROCHEMICAL GAS SENSOR WITH PASSAGE FOR RECEIVING GAS

(75) Inventors: Avinash Dalmia, Hamden, CT (US); Otto J. Prohaska, Seymour, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 785 days.

This patent is subject to a terminal disclaimer.

(21) Appl. No.: 11/070,296

(22) Filed: Mar. 2, 2005

(65) Prior Publication Data

US 2005/0147738 A1     Jul. 7, 2005

Related U.S. Application Data

(63) Continuation of application No. 10/007,234, filed on Oct. 22, 2001, now Pat. No. 6,872,290.

(51) Int. Cl.
*G01N 27/406* (2006.01)
(52) U.S. Cl. .................. 156/60; 204/409; 204/410; 204/424
(58) Field of Classification Search ............ 204/409, 204/410, 424; 156/60; 427/240
See application file for complete search history.

(56) References Cited

U.S. PATENT DOCUMENTS

| 3,608,610 | A | * | 9/1971 | Greatorex et al. ........... 159/13.1 |
| RE31,915 | E | * | 6/1985 | Oswin et al. ................. 204/412 |
| 4,795,543 | A | * | 1/1989 | Stetter et al. ................ 204/412 |
| 5,173,166 | A | * | 12/1992 | Tomantschger et al. ..... 204/412 |
| 5,431,806 | A | | 7/1995 | Suzuki et al. ................ 204/415 |
| 5,478,460 | A | | 12/1995 | Sugama et al. .............. 204/415 |
| 5,492,611 | A | | 2/1996 | Sugama et al. .............. 204/415 |
| 5,670,031 | A | | 9/1997 | Hintsche et al. ............. 204/412 |
| 6,090,268 | A | | 7/2000 | Kunimatsu et al. .......... 205/782 |

* cited by examiner

*Primary Examiner*—Kaj K Olsen
(74) *Attorney, Agent, or Firm*—St. Onge Steward Johnston & Reens LLC

(57) ABSTRACT

The invention relates to an electrochemical gas sensor having improved response time and sensitivity. The electrochemical gas sensor includes a substrate for providing a surface upon which a film of conductive material may be deposited, a pair of electrodes deposited on the substrate for permitting a measurement of current, and an electrolytic material for providing an electrical connection between the electrodes. The electrochemical gas sensor further includes a passage in the surface for holding or transporting gas received from a gas source, whereby sensing occurs at a three way interface where the gas, electrolytic material, and electrodes come in direct contact with one another.

17 Claims, 5 Drawing Sheets

ELECTROCHEMICAL GAS SENSOR WITH PASSAGE FOR RECEIVING GAS

RELATED APPLICATION

This application is a patent application for an "Electrochemical Gas Sensor with Passage for Receiving Gas." filed Oct. 22, 2001, which is a continuation of U.S. patent application Ser. No. 10/007,234, which issued Mar. 29, 2005 as U.S. Pat. No. 6,872,290.

FIELD OF THE INVENTION

The invention relates to an electrochemical gas sensor and, more particularly, to a sensor that measures gas at a triple interface point between an electrolytic material, electrode, and gas.

BACKGROUND OF THE INVENTION

Electrochemical gas sensors are typically used to determine the composition of a gas and may further be used to detect the presence of various elements or compounds in a gas.

For example, electrochemical sensors may be used in medical care equipment, such as an oxygen inhalation machine, to detect the amount of oxygen remaining in the reservoir or given to the patient. Electrochemical sensors may also be used in environmental situations for detecting the presence of dangerous chemical compounds in an unknown gas.

U.S. Pat. No. 5,431,806 ("'806 patent"), U.S. Pat. No. 5,492,611 ("'611 patent"), and U.S. Pat. No. 5,478,460 ("'460 patent") disclose an electrochemical gas sensor having a permeable membrane. These types of sensors typically measure gas by diffusing it through the membrane and dissolving it in an electrolyte on the other side of the membrane. The electrolyte is in contact with electrodes, which in turn typically measure current flow as a function of oxygen concentrations.

A disadvantage with a gas diffusion sensor is that the sensor's sensitivity is compromised. This is due to the indirect contact between the gas and the electrode or electrolyte. Gas that dissolves in the electrolyte may be carried downstream with the flow of electrolyte and may disadvantageously affect current readings and reduce sensor sensitivity. Further, the time for gas to permeate through the membrane and dissolve in the electrolyte may further negatively affect a sensor's response time.

U.S. Pat. No. 5,670,031 ("'031 patent") is directed to an electrochemical sensor having a plurality of micro electrodes in series and in close proximity to one another. This sensor typically operates by measuring differences in current flow between one pair of electrodes to the next along a length of a channel in which electrolyte flows. Because minute changes in current flow can be measured, accuracy is generally believed to be improved.

Nowhere is it claimed or disclosed in the prior art that a sensor's sensitivity can be improved by measuring the gas as it directly comes in contact with both electrolyte and electrode. The '806, '611, and '460 patents all claim a gas permeable membrane through which the gas permeates in order to be measured. The '031 patent is directed to improving the sensitivity by optimizing the contact points between the electrode and electrolyte.

Furthermore, nowhere is it claimed or disclosed in the prior art that a sensor provides a channel for transporting, holding, or receiving gas for enabling direct contact with the electrode and electrolyte for measurement.

What is desired, therefore, is to provide an electrochemical gas sensor having improved sensitivity. What is also desired is to provide an electrochemical gas sensor having an improved response time between the time gas is introduced into the sensor and when a measurement is made.

SUMMARY OF THE INVENTION

Accordingly, it is an object of the invention to provide an electrochemical gas sensor having a channel in a substrate surface, an electrode deposited on the surface, and an electrolytic material deposited on the electrode and extending over the channel for defining a passage for receiving gas.

It is also an object to provide an electrochemical gas sensor having a three way interface between gas, electrolytic material, and electrode, whereby the gas comes in direct contact with the electrolytic material and electrode.

It is a further object of the invention to provide an electrochemical gas sensor, whereby the electrolytic material is not in contact with the channel etched in the substrate.

It is still another object of the invention to provide an electrochemical gas sensor, whereby the electrode includes a thin film.

It is yet another object of the invention to provide an electrochemical gas sensor having a thin film of conductive material partially deposited within the channel.

It is yet another object of the invention to provide an electrochemical gas sensor having spin/sputter coated electrolytic material on the thin film of conductive material partially deposited within the channel.

It is yet another object of the invention to provide an electrochemical gas sensor having a thin film of conductive material completely coating the channel.

It is yet another object of the invention to provide an electrochemical gas sensor having spin/sputter coated electrolytic material on the thin film of conductive material completely coating the channel.

These and other objects of the invention are achieved by an electrochemical gas sensor having improved response time and sensitivity. The electrochemical gas sensor includes a substrate for providing a surface upon which a film of conductive material may be deposited for permitting a measurement of current, and an electrolytic material for providing an electrical connection. Electrochemical gas sensor further includes a notch in the surface for holding or transporting gas received from a gas source. Sensing occurs at a three way interface where the gas, electrolytic material, and film come in direct contact with one another.

The invention operates where the electrolytic material is not in contact with the notch, thereby defining a circumferentially closed channel formed by the notch in the surface, film deposited on the surface, and electrolytic material deposited on the film and extending over the notch.

The substrate includes known or novel materials used for forming the housing of the electrochemical gas sensor and the supporting surface upon which the film and notch are placed. The substrate has a surface that is generally, although not necessarily, flat so that a desirably thin film of conductive material may be deposited thereon. Suitable substrate materials include glass or any electrically insulating material.

The film includes a metallic material, such as platinum, for providing electrical conductivity. However, any known or novel electrically conductive material suffices. Likewise, the electrolytic material includes any material for providing an electrical connection with the film. Possible electrolytic materials include solid state polymers.

In another embodiment, the electrochemical gas sensor further includes a film of conductive material being partially deposited in the notch. The sensor also may include spin/ sputter coated electrolytic material placed on the partially deposited film for desirably increasing the quantity of three-way interfaces, thereby improving sensitivity and response time.

In another embodiment, the electrochemical gas sensor further includes a film of conductive material completely coating the notch and spin/sputter coating electrolytic material on the film for desirably increasing the quantity of three-way interfaces. This embodiment further improves sensor sensitivity and response time by maximizing the quantity of three-way interfaces within the notch. This embodiment permits sensing throughout the passage for receiving gas.

The invention and its particular features and advantages will become more apparent from the following detailed description considered with reference to the accompanying drawings.

DETAILED DESCRIPTION OF THE DRAWINGS

Figure 1:
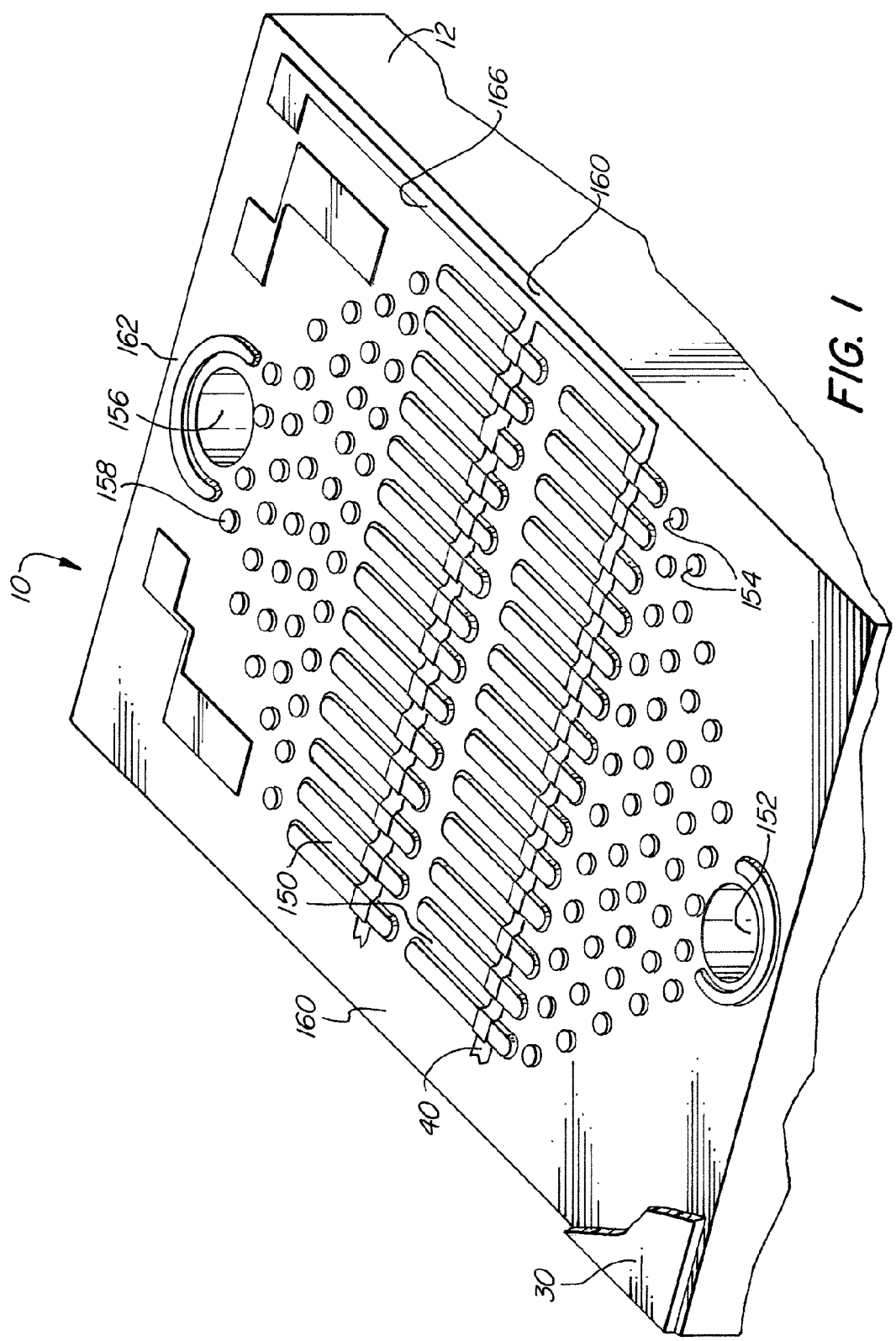
FIG. 1 depicts the electrochemical gas sensor in accordance with the invention.

FIG. 1 depicts the electrochemical gas sensor 10 in accordance with the invention. FIG. 1 depicts substrate 12, plurality of notches 150 etched in substrate 12, gas inlet 152, gas inlet dispersion posts 154, gas outlet 156, and gas outlet dispersion posts 158. Placed above and covering all the above mentioned plurality of notches 150, inlet 152, outlet 156, and posts 154, 158 is an electrolytic material 30. Electrolytic material 30, has been cut away to show the above mentioned elements lying beneath, is a flexible covering that also has sufficient rigidity so that it does not collapse into plurality of notches 150.

Plurality of notches 150 enables detection the presence of a desired gas in an unknown mixture of gases. Along each notch of plurality of notches 150, a three way interface for detecting gas between an electrolytic material, conductive material, and gas is formed. Plurality of notches 150 facilitates detection by increasing the amount of three way interfaces, thereby increasing the amount of gas that is capable of being detected. Each notch and how each individually functions is more particularly described under FIG. 2.

Unknown gas enters plurality of notches 150 through gas inlet 152. The gas is drawn through plurality of notches 150 and out through gas outlet 156. The gas is drawn from inlet 152 to outlet 156 by known or novel manners, such as vacuum, pressure differential, or any other manner for moving gas from inlet 152 through plurality of notches 150 and exiting at outlet 156.

Because gas generally travels from inlet 152 to outlet 156 via the easiest route, such as the shortest distance from inlet 152 to outlet 156, the notches at the outer portion 160, or away from the center 162 of substrate, would not be exposed to the same amount of gas as the notches toward the center 162 of substrate 12. Hence, gas inlet dispersion posts 154 are concentrated toward the center 162 of substrate 12 to provide increased resistance as opposed to the outer portion 160 of substrate 12, which has less resistance. The increased resistance causes gas to more evenly disperse across substrate 12, thereby utilizing all the notches instead of the ones in the center 162. Gas outlet dispersion posts 158 are not necessary for evenly dispersing gas across substrate 12 or for sensor 10 to function properly and are, therefore, optional. However, outlet dispersion posts 158 may be used for facilitating the egress.

The inlet and/or outlet posts, 154 and 158, include any material that protrudes upwardly from substrate 12 and is not electrically conductive because they would not inadvertently affect or participate in the electrochemical reaction of sensor 10. Insulating materials are preferred. The purpose of the inlet and outlet posts is to direct the flow of gas uniformly to all notches and/or channels. Further, the inlet and outlet posts should not have any electrochemical reaction with the gas, electrodes, or electrolytic layer. Suitable materials include glass or any other electrically insulating material. The size and other physical characteristics of the posts are not germane to the invention for the size would vary depending on a host of variables of gas flow, such as flow rate, turbulence, or temperature.

Figure 2:
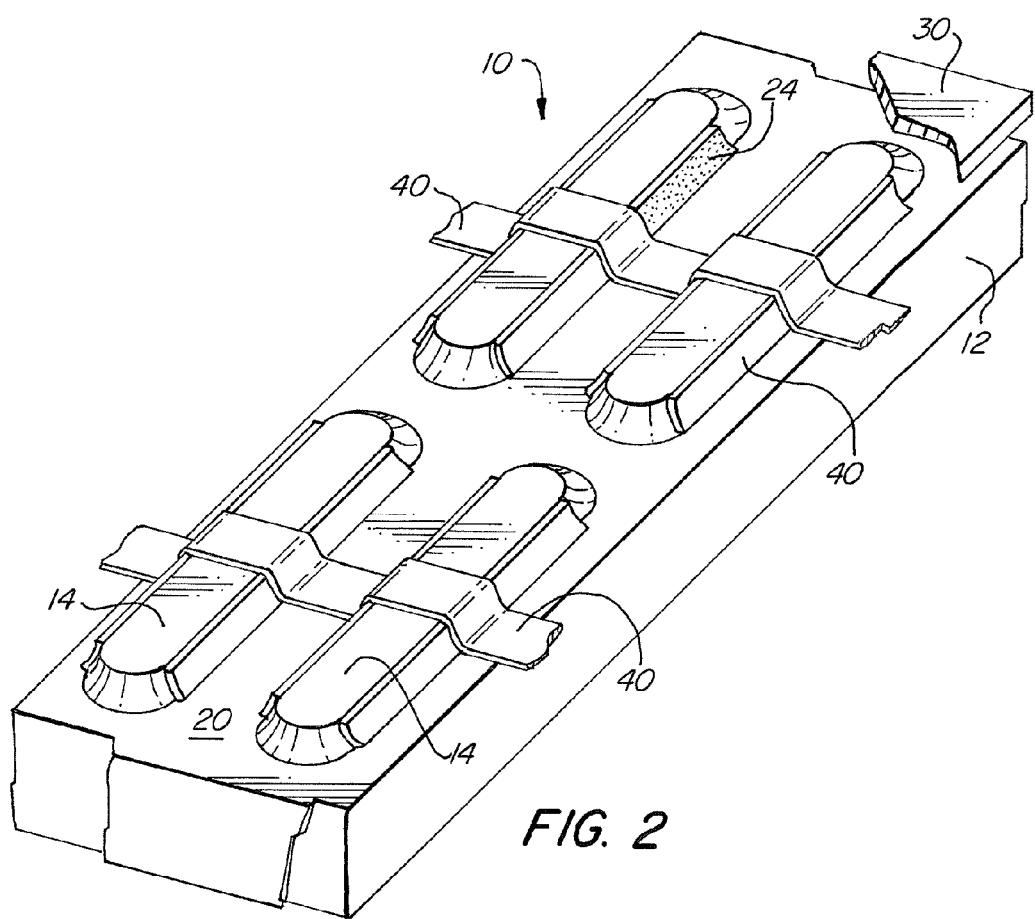
FIG. 2 depicts a close up view of the electrochemical gas sensor in accordance with the invention.

FIG. 2 shows a close up of the electrochemical gas sensor 10 depicted in FIG. 1. As opposed to plurality of notches 150 shown in FIG. 1, FIG. 2 depicts one of the plurality of notches 150. Shown in FIG. 2 is electrochemical gas sensor 10 having substrate 12, surface 14 of substrate 12, notch 20, and electrolytic material 30.

Each notch further includes electrolytic material 30, and film 40 of conductive material. As shown, film 40 is used to connect each notch to one another, including being used to form common electrical contact 166. Common electrical contact 166 enables each notch to be in electrical connection with one another, thereby permitting electrical measurements to be made as to the amount of gas present in each notch.

To provide continuous conductivity and, therefore, gas sensing among all notches, plurality of notches 150, as shown in FIG. 2, are in contact with each other by a common electrical contact 166. Common electrical contact 166 has the same limitations as film 40 and may further be the same material or any electrically conductive material.

Electrochemical gas sensor 10 operates to detect the presence of a desired gas in an unknown mixture of gases. Sensing occurs at three-way interface 24, where film 40, electrolytic material 30, and gas come in contact with one another. Further, for optimum sensitivity and response time, the contact at three-way interface 24 is direct. Meaning, gas diffusion into the electrolytic layer is minimized because the more diffusion into the electrolytic layer, the slower the response time. Moreover, the invention includes a maximized quantity of three-way interfaces 24 placed in the most desirably areas of sensor 10 for optimal sensing. As a result, sensing occurs in a plurality of areas and response time is minimized. Moreover, sensitivity is improved to be in the range of below ppb to ppb whereas conventional sensors generally do not have detection capabilities below the ppb limit.

Substrate 12 includes known or novel materials used for forming the housing of electrochemical gas sensor 10 and the supporting surface 14 upon which film 40 and notch 20 are placed. The substrate has a surface that is generally, although not necessarily, flat so that a desirably thin film of conductive material may be deposited thereon free from unnecessary pores or crevices. Suitable substrate materials include glass or any electrically insulating material.

Figure 3:
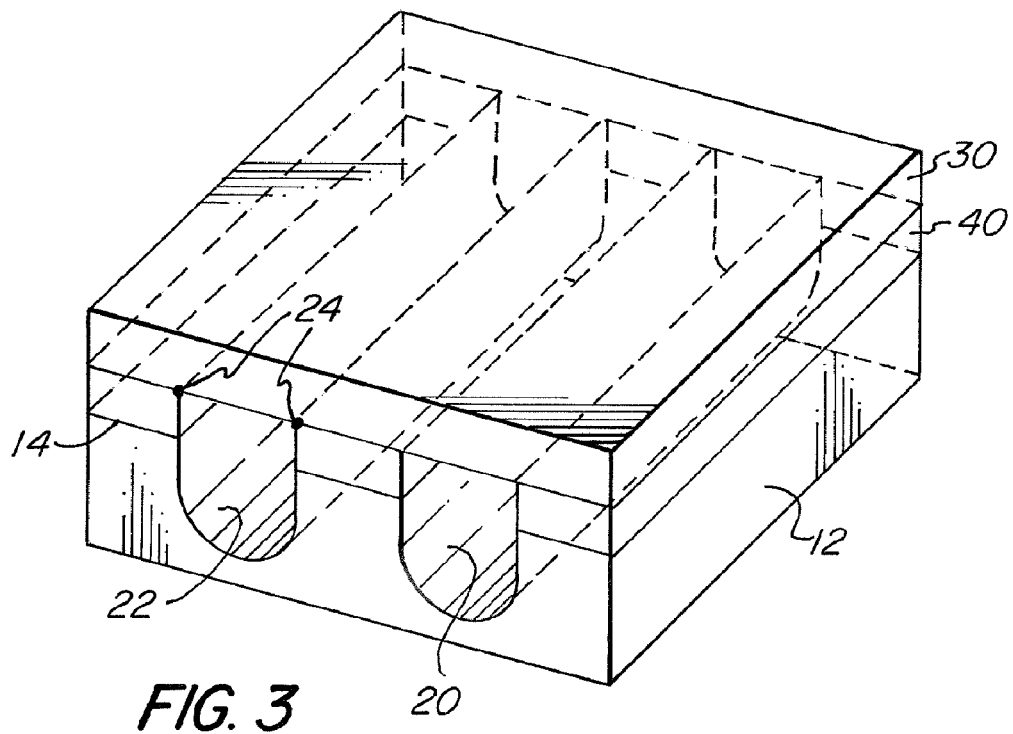
FIG. 3 depicts another close up view of the electrochemical gas sensor in accordance with the invention.
Figure 4:
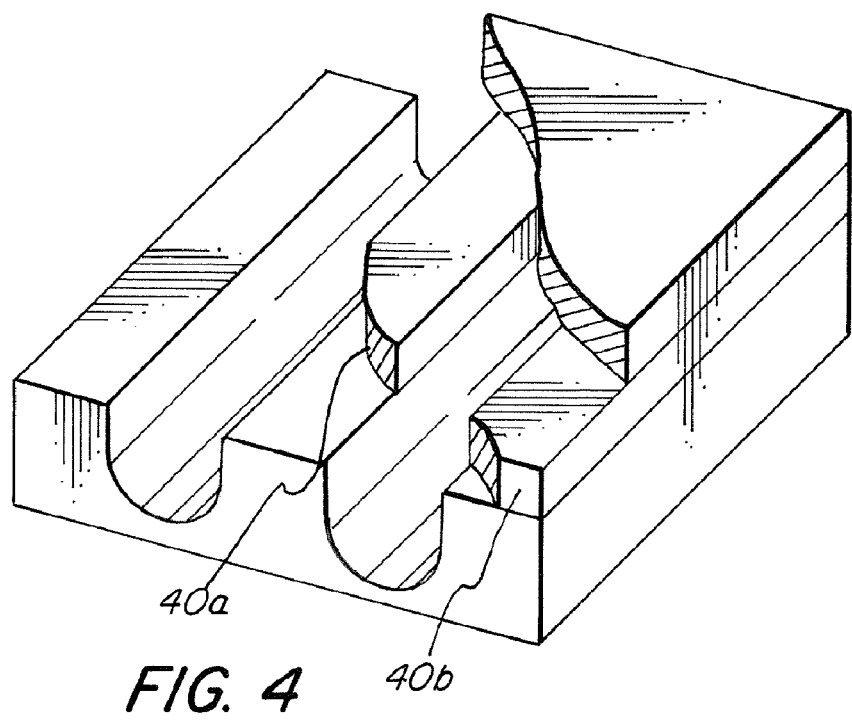
FIG. 4 more particularly depicts the individual layers used for providing the electrochemical gas sensor.

Notch 20, depicted in FIGS. 3 and 4, includes an indentation, channel, groove, or etching in substrate 12 or, more specifically, surface 14 for defining a passage for receiving gas. As depicted in FIG. 3, notch 20 is a channel within which gas is transported within electrochemical gas sensor 10 to three-way interface 24 after being received from a gas source or pump. Notch 20 may be formed or manufactured using any known or novel methods or equipment, such as machining, grinding, etching, laser cutting, or the like.

Notch 20 and surface 14 ideally, though not necessarily, have a porosity of less than 5% and a pore size not exceeding 12 microns at a pore's greatest measurement. This provides a generally smooth or polished surface upon which film 40 is deposited, thereby permitting optimal performance by the sensor. Surfaces having the above-mentioned characteristics generally permit film 40 to be deposited in a manner that has a porosity of less than 5% and a pore size not exceeding the smaller of either a width or length of film 40 at a pore's greatest measurement. Films having these characteristics operate with minimal or negligible wicking, whereby wicking is an undesirable effect of electrochemical gas sensor 10.

Film 40 of conductive material includes any known or novel electrically conductive material for permitting current flow measurement. Generally, a metallic material, such as platinum, is used for these types of materials provide sufficient conductivity. However, any known or novel material suffices so long as it is electrically conductive for permitting a measurement of current flow. Film 40 is desirably thin for reasons mentioned above which negatively affect the sensor. Film 40 acts as an electrode, whereby a pair of electrodes permits a measurement of current to be taken in order to detect gas. Film 40 may be divided into two parts, 40a and 40b, on either side of notch 20 and current may be measured across the two parts and/or between film part 40a or 40b and a counter electrode and/or between film 40 and a counter electrode. It should be noted that film 40 may be divided for current flow occurs not only across notch 20 as shown, but across any distance within electrochemical gas sensor 10 where there is a three way interface 24. As depicted more specifically in FIGS. 5 and 6, film 40 may also be deposited within the notches for providing additional three-way interfaces. Counter and reference electrodes are placed anywhere on surface 14.

Because sensing is limited to the area at or around three way interface 24, film 40 deposited in areas 172 of surface 14 not in contact with the gas is unnecessary. Areas 172 of surface 14 not in contact with gas may also electrically react with the electrolytic material that is in contact with the gas and this reaction does not positively contribute to gas detection or the positive contributions are outweighed by the noise. Non-beneficial electrical reactions, defined to be noise, therefore may be reduced by limiting film 40 to areas where there is a three way interface 24 and eliminated from areas 172 of surface 14 not in contact with gas.

Electrolytic material 30 includes a conductive medium for carrying a flow of ions or current between the pair of film parts, 40a and 40b, between either film part 40a or 40b and a counter electrode or between film 40 and a counter electrode. In sensor 10 and depicted in FIG. 1, electrolytic material 30 is in the solid state, such as Nafion. In other embodiments, electrolytic material 30 is in the liquid state. Either state is suitable for the purposes of proper functioning of electrochemical gas sensor 10. Moreover, spin/sputter coated electrolytic material 32 deposited on film 40 provides additional three-way interfaces.

Optionally, a second notch 22 may be formed in surface 14 for increasing the quantity of three-way interfaces 24 for second notch 22 provides an additional channel for receiving gas and for permitting contact between the gas, film 40, and electrolytic material 30. Similar to notch 20, second notch 22 also includes any indentation, groove, or etching in substrate 12 for defining a passage for receiving gas. Also, second notch 22 contains all the limitations as described above for notch 20, including methods of formation, porosity, and for providing a surface for depositing film 40 and electrolytic material 30 or spin/sputter coated electrolytic material 32.

Figure 5:
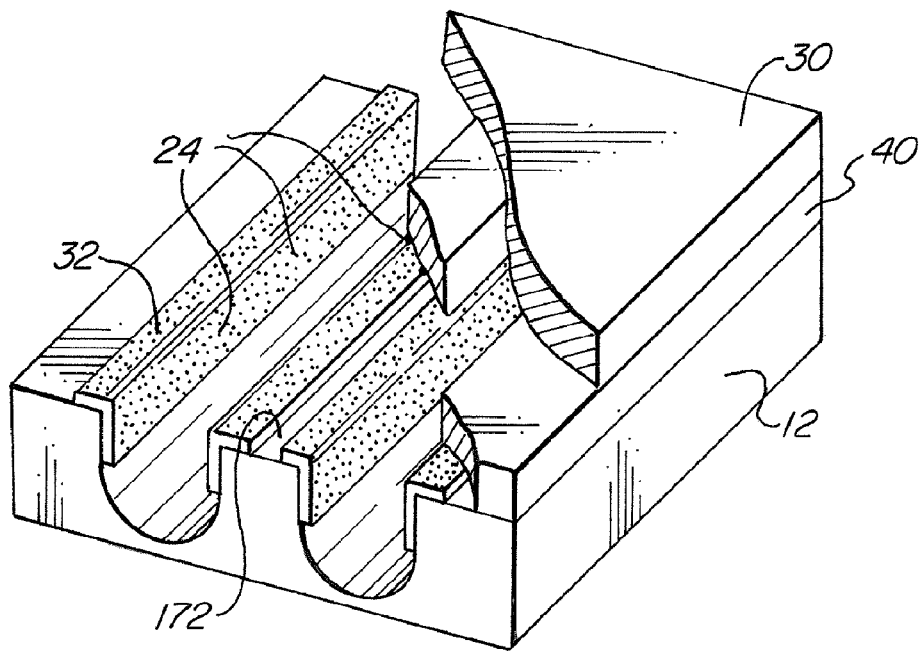
FIG. 5 depicts the electrochemical gas sensor having a film of conductive material and spin/sputter coated electrolytic material partially deposited in the passage for receiving gas.
Figure 6:
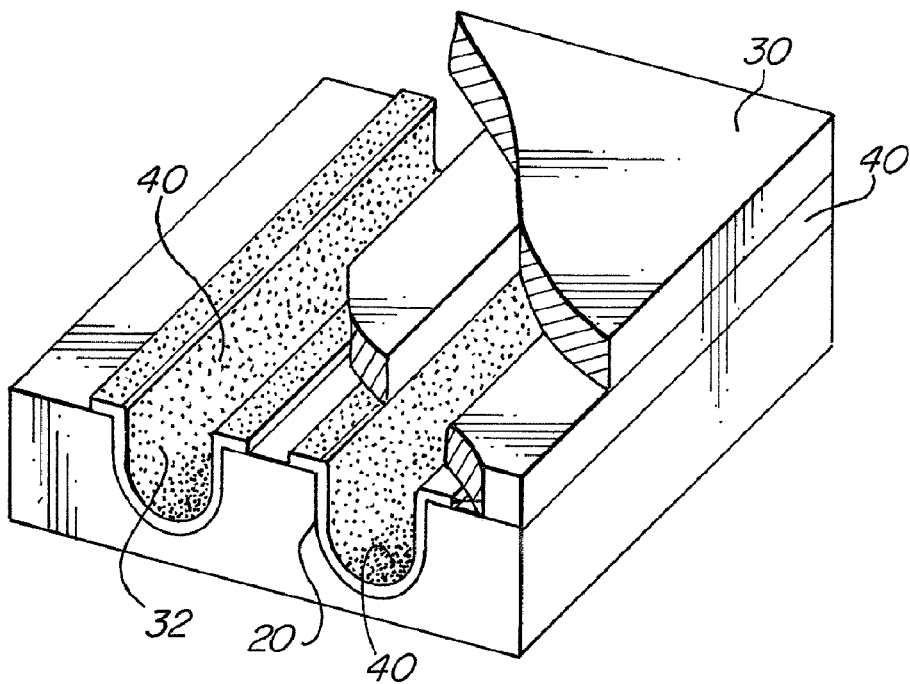
FIG. 6 depicts the electrochemical gas sensor having a film of conductive material and spin/sputter coated electrolytic material completely coating the passage for receiving gas.
Figure 7:
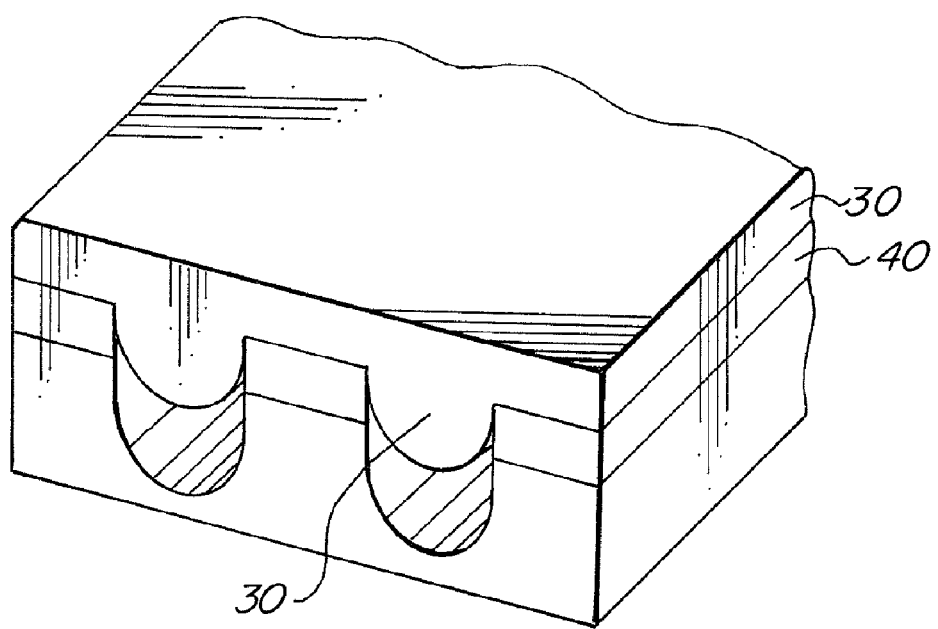
FIG. 7 depicts the electrochemical gas sensor having an electrolytic material that has expanded.

Empirical data suggests electrolytic material 30 expands during the operation of sensor 10. The expansion of electrolytic material is depicted in FIG. 7. A result of this expansion is that electrolytic material 30 tends to expand into the notch area. A disadvantage of this expansion is that, if film 40 is placed on top of surface 14 and not inside the notch, as shown in FIGS. 2, 5, and 6, the expanding electrolytic material 30 will prevent film 40, which is generally thin, from being exposed to the gas. This eliminates or disturbs the desirable three way interface 24 between electrolytic material 30, film 40, and gas. Therefore, sensing is compromised and this disadvantageously affects sensor sensitivity and response time.

A solution to the expanding electrolytic material 30 is to increase the area upon which to apply film 40. Namely, applying film within the notch. This advantage is more particularly described under FIGS. 5 and 6.

FIG. 5 depicts another embodiment of electrochemical gas sensor 10, further including film 40 of conductive material being partially deposited in notch 20 and spin/sputter coated electrolytic material 32 deposited on film 40 for desirably increasing the quantity of three-way interfaces 24. In addition to three-way interface 24 comprising of generally a line of contact along a length of notch 20 where film 40 touches electrolytic material 30, the embodiment in FIG. 5 includes film 40 and spin/sputter coated electrolytic material 32 within notch 20 for providing additional three way interfaces 24. This results in improved sensor sensitivity and response time is decreased. It should be noted that a partially deposited film may be deposited at any region of notch 20. Hence, film 40 may be deposited toward the upper region of notch 20 as depicted or on the lower region of notch 20 or on both upper and lower. Further, film 40 or spin/sputter coated electrolytic material 32 may be asymmetrically deposited or in an arbitrary manner.

FIG. 6 depicts another embodiment of electrochemical gas sensor 10, further including film 40 of conductive material completely coating notch 20 and spin/sputter coated electrolytic material 32 deposited on film 40 for desirably increasing the quantity of three-way interfaces 24. This embodiment improves upon the sensor described in FIG. 5 by maximizing the quantity of three-way interfaces 24 within notch 20. Likewise with the embodiment described in FIG. 5, film 40 and spin/sputter coated electrolytic material 32 may also be deposited within second notch 22 in the same manner as notch 20.

In addition, although two notches are depicted in FIGS. 2-7, electrochemical gas sensor 10 may include multiple notches, channels, etchings, indentations, passages, grooves, or the like. Further, each notch or a combination of notches may include film 40 and electrolytic material 30 partially or completely coating the notches. Multiple notches may be used for maximizing the quantity of three-way interfaces and further includes all the limitations as described above for each notch.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A method for providing an electrochemical sensor with a passage defined by a notch, film of electrode, and electrolytic material, comprising the steps of:
   providing a substrate having a surface;
   notching the surface to form a channel;
   placing a film of conductive electrode material over the surface such that the film is partially deposited within the channel;
   extending an electrolytic material over the film of conductive material for providing an electrical connection,
   such that the electrolytic material is not in contact with the surface of the substrate.

2. The method according to claim 1, further comprising the step of placing a gas in contact with both the film and electrolytic material.

3. The method according to claim 1, further comprising the step of spacing the electrolytic material apart from the notch.

4. The method according to claim 1, further comprising the step of providing the film as a metallic material.

5. The method according to claim 1, further comprising the step of providing the electrolytic material as a polymer.

6. The method according to claim 1, further comprising the step of providing the electrolytic material in a solid state.

7. The method according to claim 1, further comprising the step of notching the surface more than once.

8. The method according to claim 1, further comprising the step of providing the electrolytic material as Nafion.

9. The method according to claim 1, further comprising the step of placing a second film of electrode material on the notched surface.

10. The method according to claim 9, further comprising the step of placing a second electrolytic material on the second film.

11. A method for providing an electrochemical sensor, with a passage defined by a notch, first film of electrode material, second film of electrode material, and first electrolytic material, further comprising the steps of:
    providing a substrate having a surface;
    notching the surface to form a channel;
    extending a first electrolytic material over the surface for providing an electrical connection;
    placing a first film of conductive electrode material between and in direct physical contact with both the surface and first electrolytic material, such that the film is partially deposited within the channel and such that the electrolytic material is not in contact with the surface of the substrate; and
    depositing a second film of conductive electrode material on the notched surface.

12. The method according to claim 11, further comprising the step of placing a gas in contact with the notch, first film, second film, and first electrolytic material.

13. The method according to claim 11, further comprising the step of placing a second electrolytic material in contact with the second film.

14. The method according to claim 11, further comprising the step of notching the surface more than once.

15. A method for providing a electrochemical sensor with a passage defined by a notch, first film of electrode material, second film of electrode material, first electrolytic material, and second electrolytic material, comprising the steps of:
    providing a substrate having a surface;
    notching the surface to form a channel;
    extending a first electrolytic material over the surface for providing an electrical connection;
    placing a first film of electrode material between and in direct physical contact with both the surface and first electrolytic material, such that the film is partially deposited within the channel and such that the electrolytic material is not in contact with the surface of the substrate;
    depositing a second film of electrode material on the notched surface; and
    placing a second electrolytic material in contact with the second film.

16. The method according to claim 15, of placing a gas in contact with the first film, second film, and first electrolytic material, and second electrolytic material.

17. The method according to claim 15, further comprising the step of spin coating the second electrolytic material on the second film.

* * * * *